US 9,717,524 B2

(12) United States Patent
Hayashida et al.

(10) Patent No.: US 9,717,524 B2
(45) Date of Patent: Aug. 1, 2017

(54) VAGINAL CUFF CLOSURE TOOL AND METHOD

(71) Applicant: Gyrus ACMI, Inc., Southborough, MA (US)

(72) Inventors: Tsuyoshi Hayashida, Tokyo (JP); Kester J. Batchelor, Mound, MN (US)

(73) Assignee: Gyrus ACMI, Inc., Southborough, MA (US)

( * ) Notice: Subject to any disclaimer, the term of this patent is extended or adjusted under 35 U.S.C. 154(b) by 254 days.

(21) Appl. No.: 14/601,406

(22) Filed: Jan. 21, 2015

(65) Prior Publication Data

US 2015/0133947 A1   May 14, 2015

Related U.S. Application Data

(62) Division of application No. 13/804,590, filed on Mar. 14, 2013, now abandoned.

(51) Int. Cl.
| | |
|---|---|
| *A61B 17/42* | (2006.01) |
| *A61B 17/29* | (2006.01) |
| *A61B 17/00* | (2006.01) |
| *A61B 17/08* | (2006.01) |
| *A61B 17/04* | (2006.01) |

(52) U.S. Cl.
CPC ............ *A61B 17/42* (2013.01); *A61B 17/08* (2013.01); *A61B 17/29* (2013.01); *A61B 17/0469* (2013.01); *A61B 2017/00331* (2013.01); *A61B 2017/081* (2013.01); *A61B 2017/2901* (2013.01); *A61B 2017/2905* (2013.01); *A61B 2017/2906* (2013.01)

(58) Field of Classification Search
CPC .... A61B 2017/4216; A61B 2017/4225; A61B 17/42; A61B 17/4208; A61B 17/08; A61B 17/29
See application file for complete search history.

(56) References Cited

U.S. PATENT DOCUMENTS

| | | | |
|---|---|---|---|
| 5,312,391 | A | 5/1994 | Wilk |
| 5,318,013 | A | 6/1994 | Wilk |
| 5,353,784 | A | 10/1994 | Nady-Mohamad |
| 5,474,057 | A | 12/1995 | Makower et al. |
| 5,840,077 | A * | 11/1998 | Rowden ............. A61B 17/4241 606/119 |
| 8,137,263 | B2 | 3/2012 | Marescaux et al. |
| 2004/0138529 | A1 | 7/2004 | Wiltshire et al. |
| 2008/0188868 | A1 | 8/2008 | Weitzner |
| 2010/0022823 | A1 | 1/2010 | Goldfarb |
| 2012/0022334 | A1 | 1/2012 | Piskun |

FOREIGN PATENT DOCUMENTS

EP          2119402 A2    11/2009

\* cited by examiner

*Primary Examiner* — Tuan V Nguyen
(74) *Attorney, Agent, or Firm* — Vivacqua Law, PLLC; Gerald P. Kazanjian

(57) ABSTRACT

An apparatus includes a hollow sleeve member with an open interior section and a sleeve proximal and a sleeve distal end. Two or more probes are disposed within the open interior section and extending beyond the sleeve distal end when in a deployed position. Distal ends of the probes have a lateral space between each other. One or more tissue manipulators are disposed at the distal end of each of the at least two probes. The hollow sleeve member and the two or more probes move axially relative to each other to reduce the lateral space. A method of closing a vaginal cuff of a vaginal canal is also provided.

7 Claims, 7 Drawing Sheets

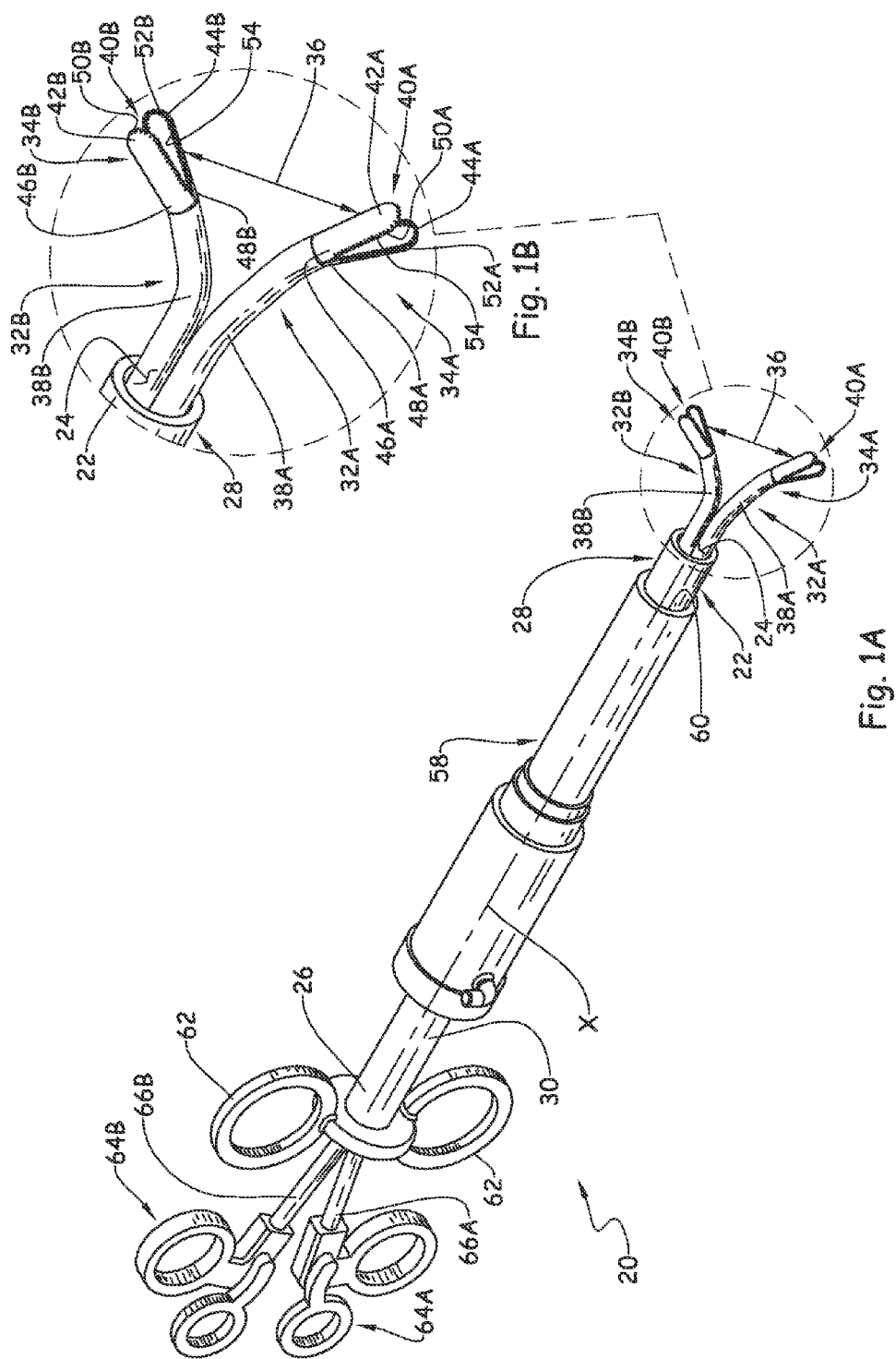

VAGINAL CUFF CLOSURE TOOL AND METHOD

RELATED APPLICATION

This application is a divisional of U.S. patent application Ser. No. 13/804,590, filed on Mar. 14, 2013 and now abandoned, the entire contents of which are incorporated herein by reference.

FIELD

The present disclosure relates to an improved tool and method for aiding in a medical procedure, more particularly to aid in a procedure where a cuff of tissue needs to be closed.

BACKGROUND

The statements in this section merely provide background information related to the present disclosure and may or may not constitute prior art.

During hysterectomy procedures, such as total laparoscopic hysterectomy (TLH) procedures, the uterus and cervix are removed, creating an approximately circular structure at end of the vaginal canal called the vaginal cuff. The closure of the remaining vaginal cuff can be one of the most challenging aspects of the procedure. It is also considered to be one of the barriers to adoption of laparoscopic surgery to those trained in open procedures.

Few devices exist to assist with closure of the vaginal cuff. The few devices that do exist relate to the suturing directly, such as Quill sutures, Covidien V Loc knotless, Ethicon Lapar Tys, and Covidien Autosuture Endostitch, by way of example. Typically, these devices do not include any assistance in the subsequent closure of the tissue to allow ease of closure and few include means to prevent escape of insufflations.

Surgeons typically use two techniques to close the cuff once they have introduced a seal against the internal walls of the vagina to reinstate insufflations in the pelvic cavity. Typically, a sponge filled glove is placed within the vaginal cavity to achieve a seal. This tends to move the often flaccid vaginal cuff into a rounder, more irregular shape.

The final closure of the cuff results in the flattening of the circular cuff opening into a flat line that is disposed transversely across the pelvis. To create the flat line, the cuff is sewn shut with sutures. Some surgeons begin suturing at one end of the eventual flat line, while others start in the middle of the final line and work to the ends. The advantage of starting at one end is reportedly that the pressure and skill required to bring the correct surfaces together are less than attempting to close in the middle. Conversely, closure in the middle allows for a more even spread of the sutures and possibly a more even distribution of sutures across the cuff closure line. While the vaginal cuff is being sutured closed, the peritoneal fold may mask the vaginal cuff opening. Furthermore, located directly above the cuff is the bladder, posing further challenges on the surgeon's skill in appropriately suturing and manipulating the suture needle without damaging the bladder.

Among the literature that can pertain to this technology include the following patent documents: U.S. Pat. No. 5,312,391; U.S. Pat. No. 5,318,013; U.S. Pat. No. 5,474,057; and U.S. Pat. No. 8,137,263, all incorporated by reference for all purposes.

Given the difficulties in correctly closing the vaginal cuff, there exists a need for tools and procedures that will aid surgeons in the process.

SUMMARY

The present disclosure provides an improved tool and method for aiding in a medical procedure, more particularly, to aid in a procedure where a cuff of tissue needs to be closed that addresses at least one or more issues described in the above paragraphs.

In one aspect, which may be combined with or separate from the other aspects described herein, the present disclosure provides an apparatus that includes a hollow sleeve member with an open interior section and a sleeve proximal and a sleeve distal end. Two or more probes are disposed within the open interior section and extending beyond the sleeve distal end when in a deployed position. Probe distal ends of the probes have a lateral space between each other. One or more tissue manipulators are disposed at the probe distal end of each of the probes. The hollow sleeve member and the two or more probes move axially relative to each other to reduce the lateral space.

In another aspect, which may be combined with or separate from the other aspects described herein, the present disclosure provides a method of closing a vaginal cuff of a vaginal canal, wherein the vaginal cuff is formed at a distal end of the vaginal canal and the vaginal canal forms a vaginal opening at a proximal end of the vaginal canal. The method includes a step of advancing a hollow sleeve member with an open interior section and a sleeve proximal and a sleeve distal end into a patient's anatomy. The method also includes a step of advancing a first probe and a second probe through the open interior section of the hollow sleeve member and into the patient's anatomy through the sleeve distal end, wherein the first probe has a first tissue manipulator disposed at a probe distal end of the first probe and the second probe has a second tissue manipulator disposed at a probe distal end of the second probe. The method further includes a step grasping a first tissue portion of the vaginal cuff with the first tissue manipulator and grasping a second tissue portion of the vaginal cuff with the second tissue manipulator, wherein the first and second tissue portions are spaced apart from each other by a lateral space. In addition, the method includes a step of moving at least one of the hollow sleeve member and the first and second probes relative to each other to reduce or eliminate the lateral space.

Accordingly, pursuant to one aspect of the invention, there is contemplated an apparatus comprising one or more of the following: a hollow sleeve member with an open interior section and a sleeve proximal and a sleeve distal end; two or more probes disposed within the open interior section and extending beyond the sleeve distal end when in a deployed position and wherein probe distal ends of the probes have a lateral space between each other; one or more tissue manipulators disposed at the probe distal end of each of the probes; and wherein the hollow sleeve member and the two or more probes move axially relative to each other to reduce the lateral space.

Accordingly, pursuant to another aspect of the invention, there is contemplated a method of closing a vaginal cuff of a vaginal canal, the vaginal cuff being formed at a distal end of the vaginal canal and the vaginal canal forming a vaginal opening at a proximal end of the vaginal canal, the method comprising one or more of the following steps: advancing a hollow sleeve member with an open interior section and a sleeve proximal and a sleeve distal end into a patient's anatomy; advancing a first probe and a second probe through the open interior section of the hollow sleeve member and into the patient's anatomy through the sleeve distal end, the first probe having a first tissue manipulator disposed at a probe distal end of the first probe and the second probe having a second tissue manipulator disposed at a probe distal end of the second probe; grasping a first tissue portion of the vaginal cuff with the first tissue manipulator and grasping a second tissue portion of the vaginal cuff with the second tissue manipulator, the first and second tissue portions being spaced apart from each other by a lateral space; and moving at least one of the hollow sleeve member and the first and second probes relative to each other to reduce or eliminate the lateral space.

The invention may be further characterized by one or any combination of the features described herein, such as: the hollow sleeve member is configured to be advanced into a patient's anatomy to reduce the lateral space between the distal ends of the two (or more) probes; the two or more probes are flexible; each of the probes has a distal end portion disposed at the probe distal end, the distal end portion being preformed into a preformed arcuate shape; the hollow sleeve member defines a longitudinal axis extending along the length of the hollow sleeve member through the open interior section; the probe distal end of each probe is disposed a distance apart from the longitudinal axis when the probe distal end of each probe extends beyond the sleeve distal end in the deployed position; the probe distal end of each probe extends at an angle of at least 30 degrees from the longitudinal axis when the probe distal end of each probe extends beyond the sleeve distal end in the deployed position; each tissue manipulator includes a grasper having first and second parts that are hinged together at proximal ends of the first and second parts; each first part has a first toothed side and each second part has a second toothed side, the first and second toothed sides configured to mate together; each probe is configured to move axially with respect to one another; the probes have an individually movable state and a fixed together state; each probe of the is configured to move axially with respect to one another in the individually moveable state, and the probes are attached together in the fixed together state; the apparatus further comprises an outer cannula; the hollow sleeve member is axially moveable along the longitudinal axis with respect to the outer cannula; the step of moving the hollow sleeve member and/or the first and second probes relative to each other comprises advancing the hollow sleeve member over the first and second probes, thereby bringing together the probe distal ends of the first and second probes and the first and second tissue portions to reduce or eliminate the lateral space; the step of moving at least one of the hollow sleeve member and the first and second probes relative to each other comprises advancing the hollow sleeve member toward the vaginal cuff over the first and second probes; inserting the outer cannula into the patient's anatomy; the step of advancing the hollow sleeve member includes advancing the hollow sleeve member through the outer cannula, wherein advancing the hollow sleeve member toward the vaginal cuff over the first and second probes includes moving the hollow sleeve member axially with respect to the outer cannula; the vaginal cuff defines a vaginal cuff plane; the first and second tissue portions are disposed generally within the vaginal cuff plane; holding the first and second probes with respect to the outer cannula after grasping the first and second tissues portions and keeping the first and second tissue manipulators generally within the vaginal cuff plane when the hollow sleeve member is advanced over the first and second probes; suturing the first and second tissue portions together while holding the first and second tissue portions together with the first and second tissue manipulators; the step of suturing includes beginning the suturing by fixing a first suture through a first central portion of the first tissue portion and a second central portion of the second tissue portion, thereby connecting the first and second central portions together, the first and second central portions being disposed on opposite sides of the vaginal cuff; and the step of advancing the hollow sleeve member into the patient's anatomy includes advancing the hollow sleeve member into the vaginal canal through the vaginal opening.

Further aspects, advantages and areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIG. 1A is a perspective view of an apparatus for aiding in the closure of a vaginal cuff, in accordance with the principles of the present disclosure; FIG. 1B is an enlarged perspective view of a portion of the apparatus of FIG. 1A, according to the principles of the present disclosure;

DETAILED DESCRIPTION

Figure 2A:
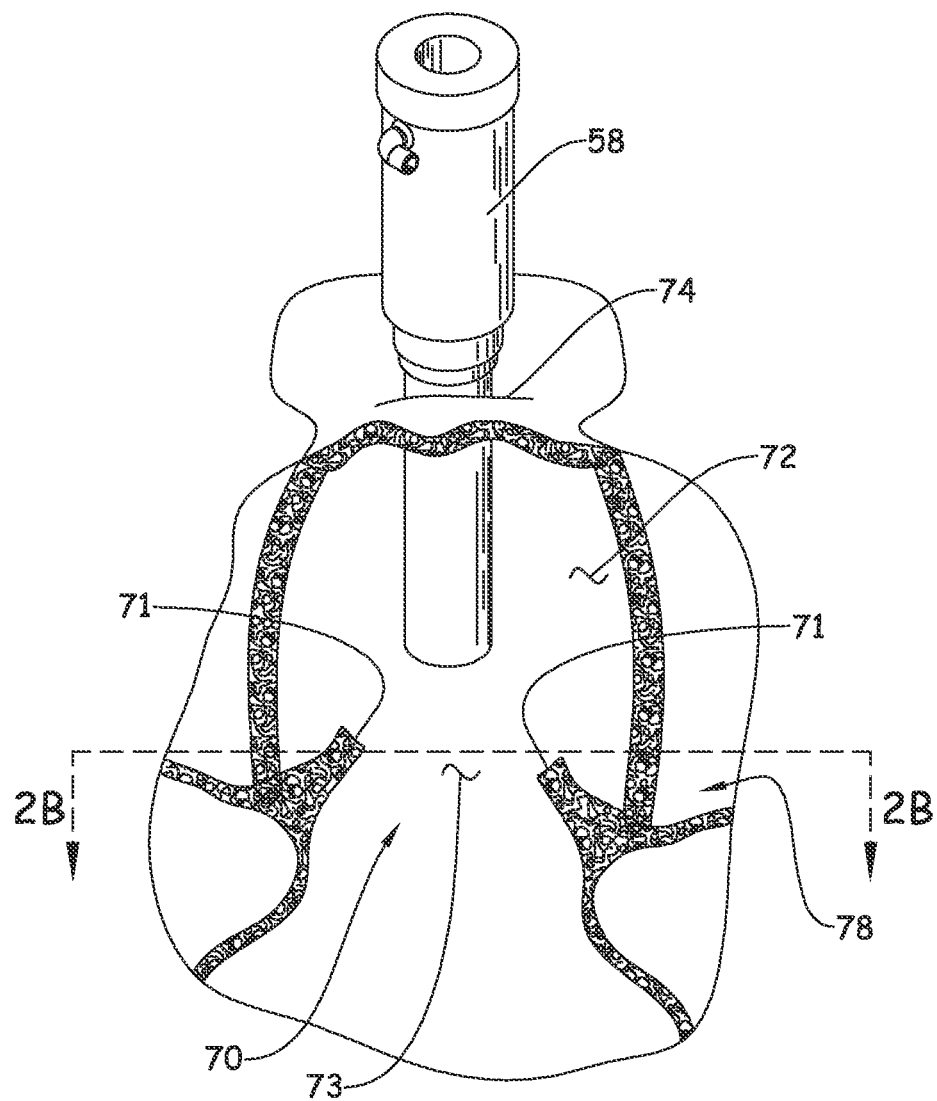
FIG. 2A is a cross-sectional side view of a vaginal canal and a vaginal cuff, having a portion of an outer cannula inserted into the vaginal canal, according to the principles of the present disclosure.

The following description is merely exemplary in nature and is not intended to limit the present disclosure, application, or uses. The present invention relates to a vaginal cuff closure tool and method.

With reference to the figures, wherein like numerals indicate like components, and specifically with reference to FIGS. 1A and 1B, an example of an apparatus in accordance with the principles of the present disclosure is illustrated and generally designated at 20. The apparatus 20 may be used to aid in the closure of a vaginal cuff after cervix removal, such as after a hysterectomy. The apparatus 20 may be inserted into a patient's vaginal canal through the vaginal opening, or the apparatus may be inserted laparoscopically through an incision.

The apparatus 20 has a hollow sleeve member 22 with an open interior section 24. The sleeve member 22 has a sleeve proximal end 26 and a sleeve distal end 28, with a main body portion 30 extending between the proximal end 26 and the distal end 28. The sleeve member 22 may be an elongate hollow tube, which is rigid or semi-rigid, as shown in FIGS. 1A and 1B.

Two or more probes 32A, 32B are at least partially disposed within the open interior section 24. In the illustrated example, the probes 32A, 32B extend beyond both the sleeve proximal end 26 and the sleeve distal end 28 when in a deployed position near the vaginal cuff of a patient, which will be described in further detail below. When not deployed, or when partially deployed, the probes 32A, 32B may be disposed within the sleeve member 22 such that the probes 32A, 32B do not extend beyond the distal end 28 of the sleeve member 22.

When the apparatus 20 is deployed near the patient's vaginal cuff, distal ends 34A, 34B of the probes 32A, 32B have a lateral space 36 between each other. In the illustrated embodiment, the distal ends 34A, 34B have the lateral space 36 between each other when the distal ends 34A, 34B extend beyond the distal end 28 of the sleeve member and when the distal ends 34A, 34B of the probes 32A, 32B are located outside of the interior section 24 of the sleeve member 22. Distal end portions 38A, 38B of the probes 32A, 32B may be preformed into a preformed arcuate shape as shown in FIGS. 1A and 1B. The distal end portions 38A, 38B are located at the distal ends 34A, 34B of the probes 32A, 32B.

The hollow sleeve member 22 defines a longitudinal axis X extending along the length of the hollow sleeve member 22 through the open interior section 24. The distal end 34A, 34B of each probe 32A, 32B is disposed a distance apart from the longitudinal axis X (half of distance of the lateral space 36 between the distal ends 34A, 34B when the distal end 34A, 34B of each probe 32A, 32B extends beyond the sleeve distal end 28 in the deployed position. In one embodiment, the distal end 34A, 34B of each probe extends at an angle $\alpha_A$, $\alpha_B$ of at least 30 degrees from the longitudinal axis X when the distal end 34A, 34B of each probe 32A, 32B extends beyond the sleeve distal end 28 in the deployed position. In other embodiments, however, the angles $\alpha_A$, $\alpha_B$ could be less than 30 degrees.

When the distal end portions 38A, 38B are disposed in the hollow sleeve member 22, the distal end portions 38A, 38B may be compressed into a straight, or straighter shape. The distal end portions 38A, 38B may then be configured to take on their preformed arcuate shape when the distal end portions 38A, 38B are located outside the hollow sleeve member 22. In other words, distal end portions 38A, 38B may be configured to return to their arcuate preformed shape so long as another force is not bending the distal end portions 38A, 38B out of their arcuate preformed shape. Therefore, the probes 32A, 32B are flexible to move between an expanded state (when deployed) and a collapsed state (when located in the sleeve member 22).

For example, the probes may be formed of a shape memory material, such as Nitinol. Shape memory materials or alloys have the desirable property of becoming rigid, i.e., returning to a remembered state, when heated above a transition temperature. When this material is heated above the transition temperature, the material undergoes a phase transformation from martensite to austenite, such that the material returns to its remembered state. The Nitinol could be of various types, such as linear elastic Nitinol. The probes 32A, 32B could be made from shape memory material having a transition temperature that is below normal body temperature of humans, which is about 98.6° F. Thus, when the tubular probes 32A, 32B are deployed in the patient's body and exposed to normal body temperature, the alloy of the probes 32A, 32B will return to their remembered state, which for one embodiment is the expanded, preformed arcuate state.

Thus, the probes 32A, 32B are configured to move between an expanded state for attaching to the open vaginal cuff, and a collapsed state when pressed or otherwise collapsed into a straight shape in the sleeve member 22. The probes 32A, 32B are configured to open radially to define the expanded state and to collapse along a central longitudinal axis X, which extends through the sleeve member 22, to define the collapsed state. The probes 32A, 32B may be self-expanding, for example, through a spring force contained in the probes 32A, 32B.

One or more tissue manipulators, such as graspers 40A, 40B are disposed at the distal end 34A, 34B of each of probe 32A, 32B. The graspers 40A, 40B are configured to grasp edges of the open vaginal cuff, which will be described in further detail below. The graspers 40A, 40B may be connected to a wire or other control device (not shown) that extends through the probes 32A, 32B for controlling the graspers 32A, 32B. The graspers 40A, 40 each have a first part 42A, 42B and a second part 44A, 44B. The first part 42A, 42B and the second part 44A, 44B are hinged together at a pivot point, which may have a pivot pin (not shown) that is located at proximal ends 46A, 46B, 48A, 48B of the first and second parts 42A, 42B, 44A, 44B. Each first part 42A, 42B has a first toothed side 50A, 50B and each second part 44A, 44B has a second toothed side 52A, 52B. The first and second toothed sides 50A, 50B, 52A, 52B are configured to mate together to grip tissue. Each toothed side 50A, 50B, 52A, 52B bears a plurality of teeth 54.

An outer cannula 58 is disposed around the sleeve member 22. The outer cannula 58 has a cylindrical, tubular shape and defines a channel 60 therethrough. The sleeve member 22 is disposed in the channel 60 of the outer cannula 58. The hollow sleeve member 22 is axially moveable along the longitudinal axis X with respect to the outer cannula 58, within the channel 60 of the outer cannula 58.

Control handles 62 are attached to the proximal end 26 of the sleeve member 22 to move the sleeve member 22 axially with respect to the outer cannula 58 along the longitudinal axis X. It is contemplated that the outer cannula 58 will remain in a fixed position with respect to a patient's anatomy, which will be described in further detail below.

Another pair of control handles 64A, 64B is attached to proximal ends 66A, 66B of the probes 32A, 32B. The control handles 64A, 64B are used to move the probes 32A, 32B with respect to the sleeve member 22, along the longitudinal axis X or along a line parallel to the longitudinal axis X. The probes 32A, 32B may be configured to move axially with respect to one another, or the probes 32A, 32B may be configured to move together. For example, the probes 32A, 32B may have an individually movable state and a fixed together state, wherein each probe 32A, 32B is configured to move axially with respect to one another in the individually moveable state, and wherein the probes 32A, 32B are attached together in the fixed together state. The probes 32A, 32B may also be moved together axially without being attached together.

Figure 2B:
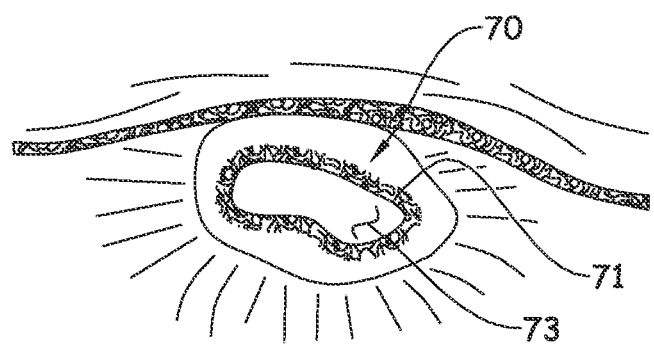
FIG. 2B is a cross-sectional end view of the vaginal cuff of FIG. 2A, in accordance with the principles of the present disclosure.

Referring now to FIGS. 2A, 2B and 3-5, use of the apparatus 20 to close the vaginal cuff 70 of a patient is illustrated. As shown in FIGS. 2A-2B, the patient's uterus and cervix have been removed, creating an approximately circular structure at a distal end 78 of the vaginal canal 72 called the vaginal cuff 70. The vaginal cuff 70 has an approximately round or oval circumference edge 71 defining an opening 73. It is desirable to close the opening 73 of the vaginal cuff 70.

In the illustrated embodiment, the outer cannula 58 is inserted to in the vaginal canal 72 through the vaginal opening 74. In the alternative, the outer cannula 58 may be inserted into the patient laparoscopically through an incision. The outer cannula 58 is maintained in a fixed position with respect to the patient's anatomy, including with respect to the vaginal cuff 70, in this example.

Figure 3:
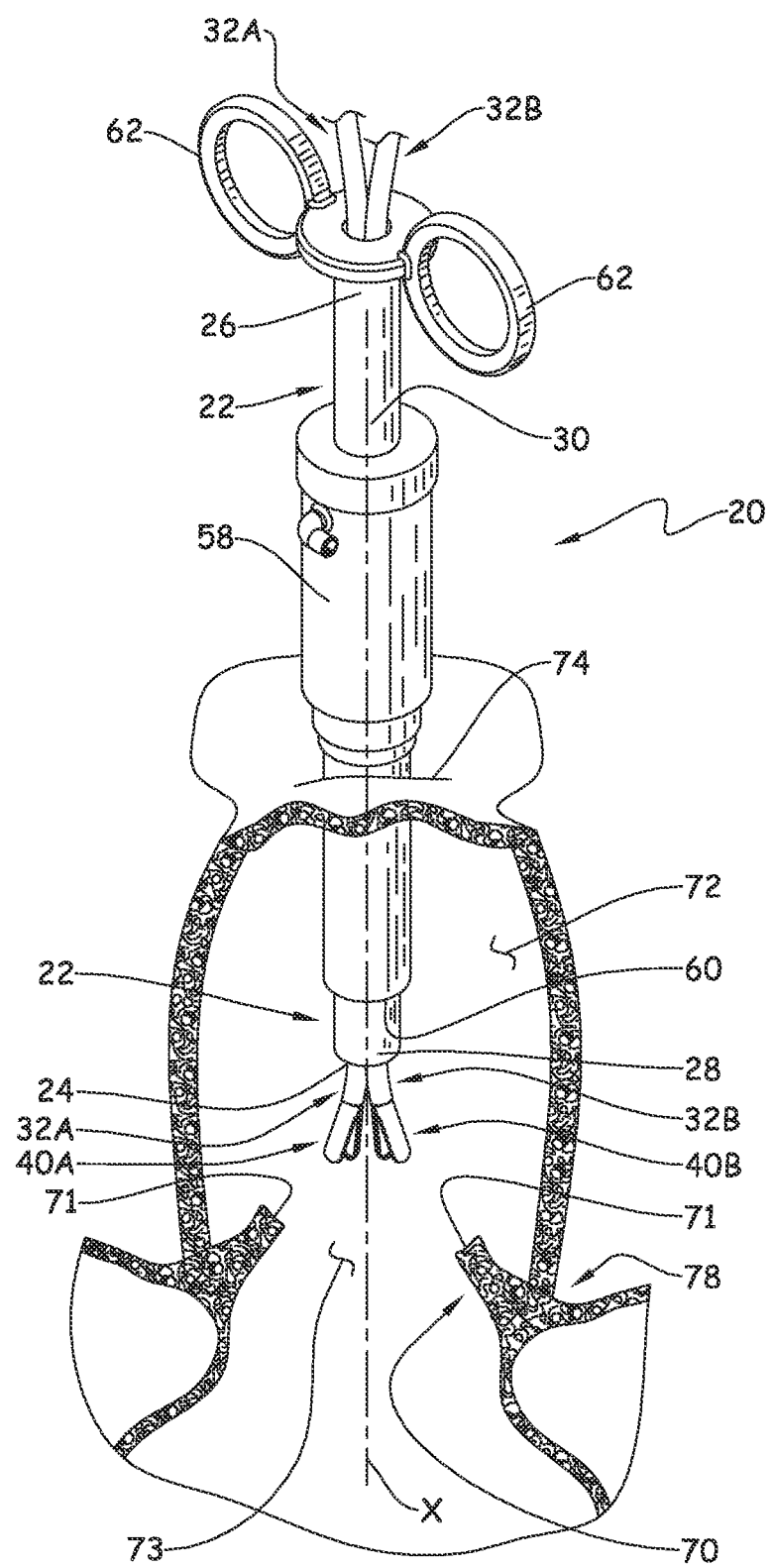
FIG. 3 is a cross-sectional side view of the vaginal canal and the vaginal cuff of FIGS. 2A-2B, having the apparatus of FIG. 1A inserted into the vaginal canal, including inserting a hollow sleeve member and probes through the outer cannula of FIG. 2A, according to the principles of the present disclosure.

Referring to FIG. 3, the sleeve member 22 and the probes 32A, 32B have been inserted into the vaginal canal 72 through the outer cannula 58. The sleeve member 22 is configured to move axially along the longitudinal axis X, as are the probes 32A, 32B (or along a line parallel to the longitudinal axis X), with respect to the outer cannula 58.

Figure 4:
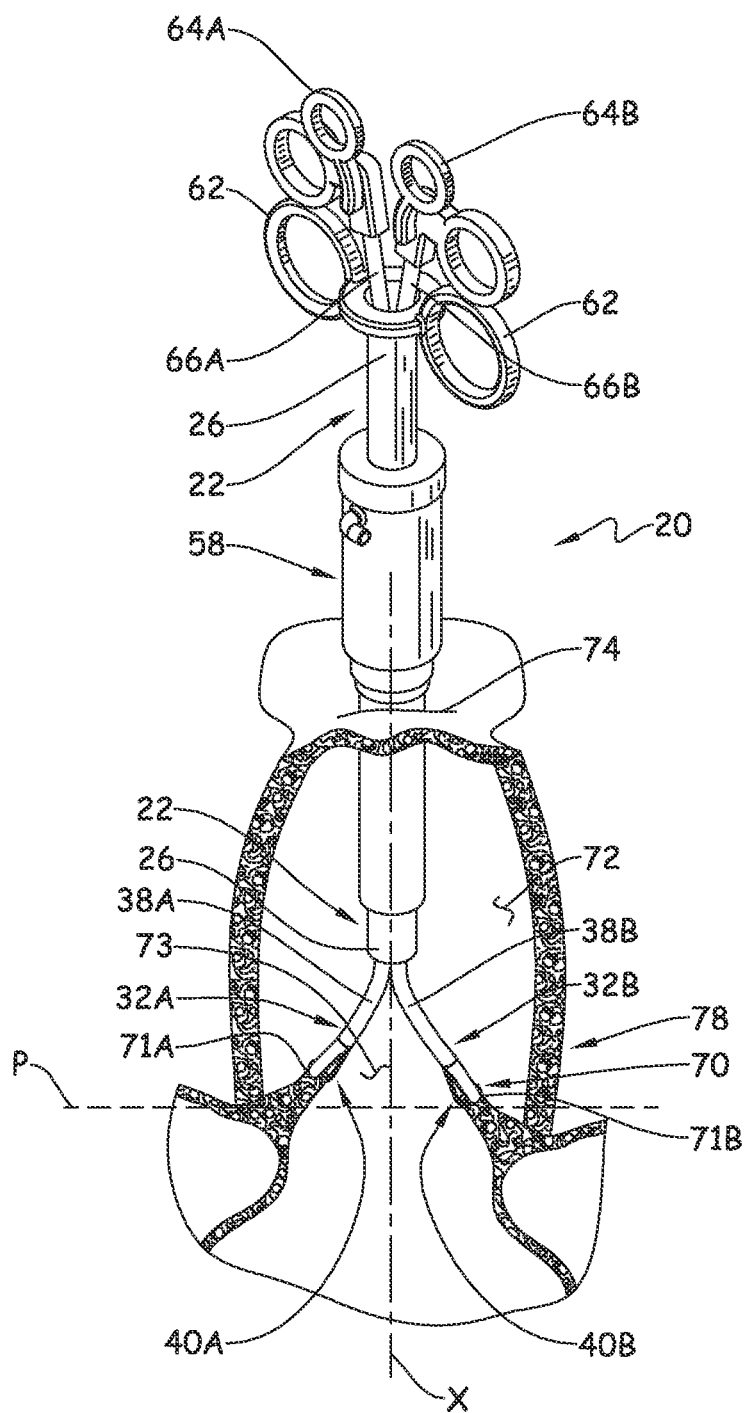
FIG. 4 is a cross-sectional side view of the vaginal canal and the vaginal cuff of FIGS. 2A-2B an 3, having the apparatus of FIGS. 1A and 3 inserted into the vaginal canal, with the probes grasping portions of the vaginal cuff, in accordance with the principles of the present disclosure.

Referring now to FIG. 4, the probes 32A, 32B have been advanced into the vaginal canal 72 through the sleeve member 22. The distal end portions 38A, 38B of the probes 32A, 32B have been moved axially out of the sleeve member 22. Each probe 32A, 32B has automatically curved outwardly from the longitudinal axis X to take on the preformed curved shapes of the probes 32A, 32B. Thus, the probes 32A, 32B extend at angles $\alpha_A$, $\alpha_B$ with respect to the longitudinal axis X. In other embodiments, however, the probes 32A, 32B need not have the preformed curved shape. The graspers 40A, 40B have each been attached to the circumference edge 71 of the vaginal cuff 70 at locations on the circumference edge 71 that are approximately opposite each other along a diameter of the opening 73 of the vaginal cuff 70.

Figure 5:
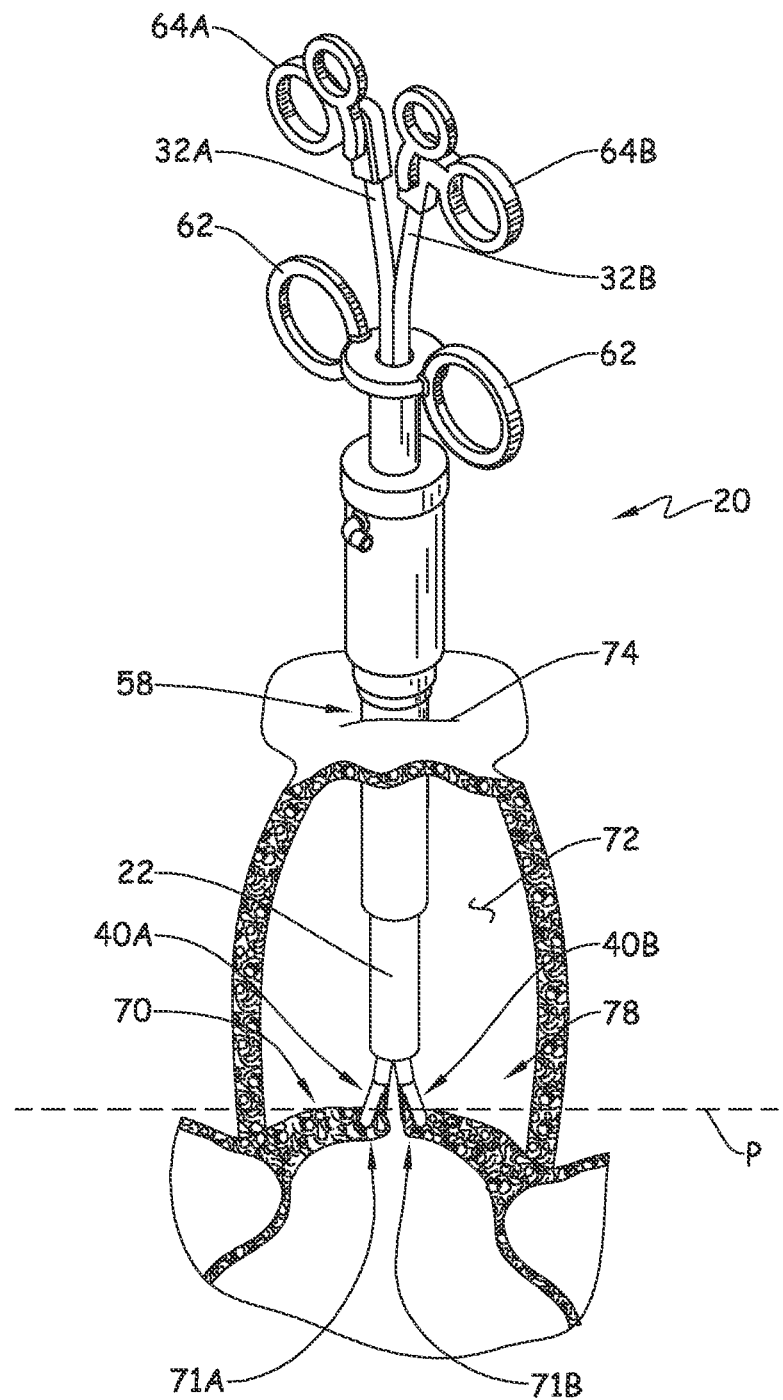
FIG. 5 is a cross-sectional side view of the vaginal canal and the vaginal cuff of FIGS. 2A-2B an 3, having the apparatus of FIGS. 1A, 3, and 4 inserted into the vaginal canal, with the probes grasping portions of the vaginal cuff, and portions of the cuff being brought together, in accordance with the principles of the present disclosure.

With reference to FIG. 5, an illustration of how the apparatus 20 assists in closing the vaginal cuff 70 is provided. After the graspers 40A, 40B have been attached to opposite portions of the circumference edge 71 of the vaginal cuff 70, as shown in FIG. 4, the apparatus 20 is used to bring together the graspers 40A, 40B to pull the opposite portions of the circumference edge 71 together in a lateral direction that is perpendicular to the longitudinal axis X.

In the illustrated example, the sleeve member 22 has been advanced axially toward the vaginal cuff 70 along the longitudinal axis X, and the outer cannula 58 and the probes 32A, 32B have been maintained in an axially fixed position in the direction of the longitudinal axis X. By virtue of the sleeve member 22 advancing over the probes 32A, 32B when the sleeve member 22 is moved axially toward the cuff 70, the probes 32A, 32B move toward each other along a transverse plane that is perpendicular to the longitudinal axis X. Thus, the probes 32A, 32B are moved toward each other to reduce the lateral space 36 between the distal ends 34A, 34 of the probes 32A, 32B.

In one example, the vaginal cuff 70 defines a vaginal cuff plane P. First and second tissue portions 71A, 71B of the circumference edge 71 of the vaginal cuff 70 are disposed generally within the vaginal cuff plane P. The first and second probes 32A, 32B are held with respect to the outer cannula 58 after the graspers 40A, 40B are attached to the first and second tissues portions 71A, 71B. The hollow sleeve member 22 is then advanced over the probes 32A, 32B while keeping the graspers 40A, 40B generally within the vaginal cuff plane P. Therefore, the first and second tissue portions 71A, 71B are pulled together generally along the cuff plane P in a lateral direction, while substantially avoiding stretching the tissue portions 71A, 71B in other directions, such as along the longitudinal axis X.

Figure 6:
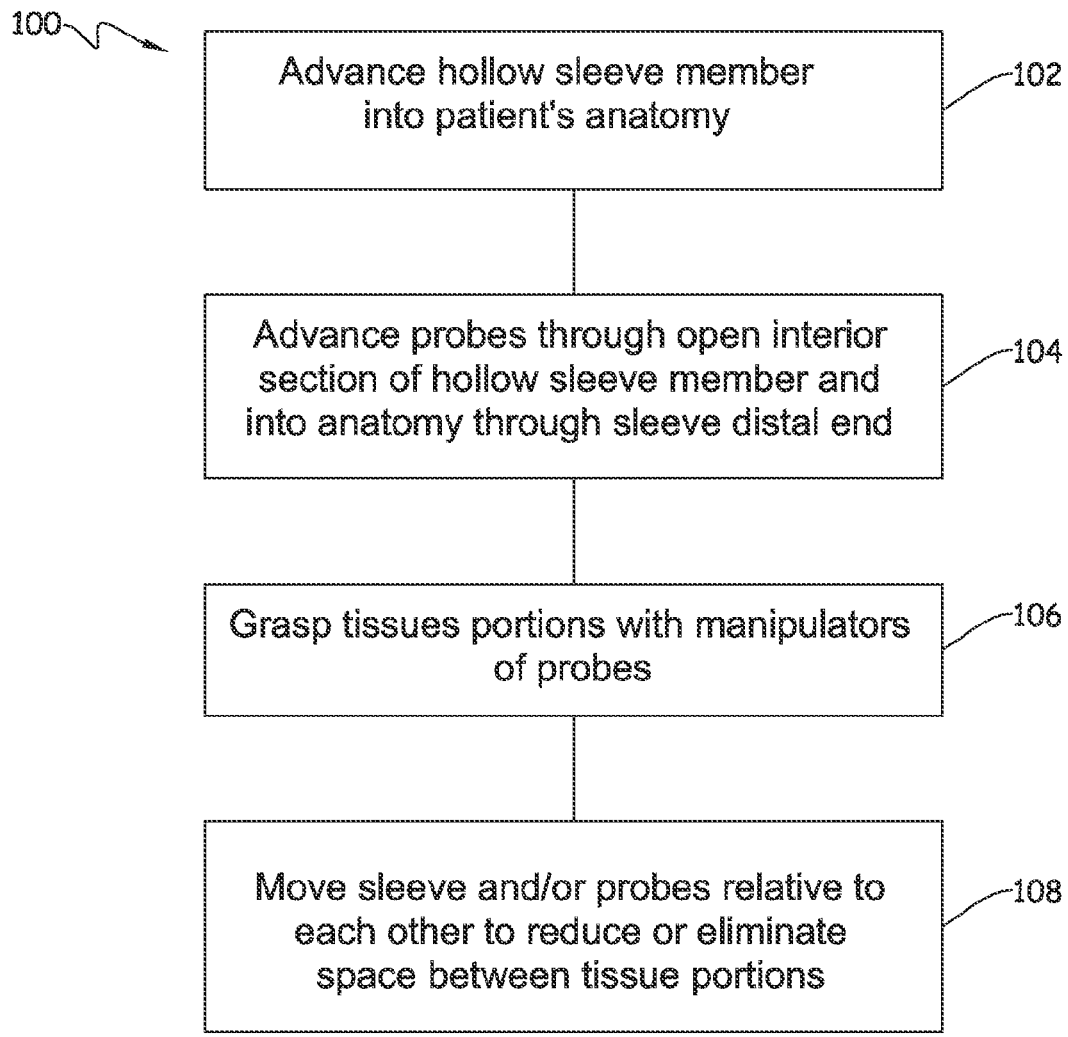
FIG. 6 is a block diagram illustrating a method of closing a vaginal cuff, according to the principles of the present disclosure.

Referring to FIG. 6, along with FIGS. 2A-2B and 3-5, a method 100 of closing the vaginal cuff 70 of the vaginal canal 72 is provided. The method 100 includes a step 102 of advancing the hollow sleeve member 22 into a patient's anatomy; an example of this step 102 is illustrated in FIG. 3.

The method 100 also includes a step 104 of advancing the first probe 32A and the second probe 32B through the open interior section 24 of the hollow sleeve member 22 and into the patient's anatomy through the sleeve distal end 28. As described above, the first probe 32A may have a first tissue manipulator 40A disposed at a distal end 34A of the first probe 32A, and the second probe 32B may have a second tissue manipulator 40B disposed at a distal end 34B of the second probe 32B.

The method 100 could further include a step 106 of grasping the first tissue portion 71A of the vaginal cuff 70 with the first tissue manipulator 40A and grasping the second tissue portion 71B of the vaginal cuff 70 with the second tissue manipulator 40B. The first and second tissue portions 71A, 71B are spaced apart from each other by a lateral space 36. This step 106 is illustrated in FIG. 4.

The method 100 may then include a step 108 of moving at least one of the hollow sleeve member 22 and the first and second probes 32A, 32B relative to one another to reduce or eliminate the lateral space 36. This step 108 is illustrated in FIG. 5. As shown in FIG. 5, this step 108 could include advancing the hollow sleeve member 22 over the first and second probes 32A, 32B, thereby bringing together the distal ends 34A, 34B of the first and second probes 32A, 32B and the first and second tissue portions 71A, 71B to reduce or eliminate the lateral space 36, while maintaining the tissue portions 71A, 71B substantially within the original cuff plane P. Thus, this step 108 could include advancing the hollow sleeve member 22 toward the vaginal cuff 70 over the first and second probes 32A, 32B.

The method 100 could also include a step of inserting the outer cannula 58 into the patient's anatomy as shown in FIG. 2A. The step 102 of advancing the hollow sleeve member 22 may include advancing the hollow sleeve member 22 through the channel 60 of the outer cannula 58, such that advancing the hollow sleeve member 22 toward the vaginal cuff 70 over the first and second probes 32A, 32B includes moving the hollow sleeve member 22 axially with respect to the outer cannula 58. Accordingly, the step of inserting the outer cannula 58 into the patient's anatomy could occur before advancing the sleeve member 22 into the patient's anatomy.

As explained above, the vaginal cuff 70 defines a vaginal cuff plane P, and the first and second tissue portions 71A, 71B are disposed generally within the vaginal cuff plane P. The method 100 could further include a step of holding the first and second probes 32A, 32B with respect to the outer cannula 58 after grasping the first and second tissues portions 71A, 71B and keeping the first and second tissue manipulators 40A, 40B generally within the vaginal cuff plane P when the hollow sleeve member 22 is advanced over the first and second probes 32A, 32B.

Figure 7A:
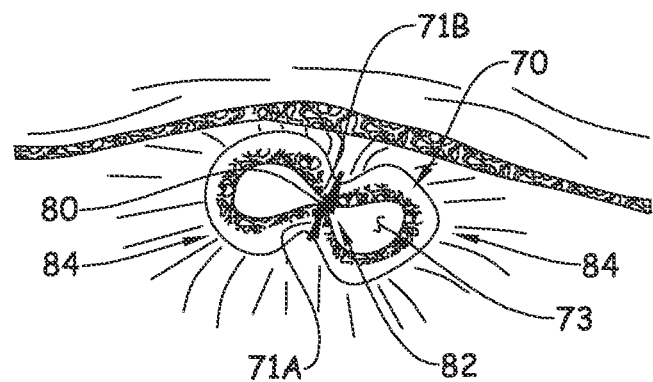
FIG. 7A is a cross-sectional end view of the vaginal cuff of FIG. 2A, having a suture sewn centrally therethrough, in accordance with the principles of the present disclosure.
Figure 7B:
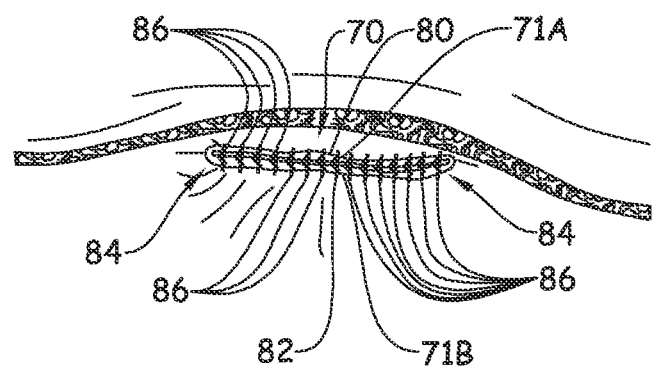
FIG. 7B is a cross-sectional end view of the vaginal cuff of FIGS. 2A and 7A, having a plurality of sutures sewn therethrough, according to the principles of the present disclosure.

Referring now to FIGS. 7A-7B, the method 100 could further include suturing the first and second tissue portions 71A, 71B together while holding the first and second tissue portions together 71A, 71B with the first and second tissue manipulators 40A, 40B. As the tissue portions 71A, 71B are held together, adjacent to each other and touching each other as shown in FIG. 5, a single suture 80 is placed around the cuff opening 73 through the first and second tissue portions 71A, 71B. The first suture 80 is placed centrally through the middle 82 of the cuff 70 through a first central tissue portion 71A and a second central tissue portion 71B. In the alternative, suturing could start at a side 84 of the opening 73, thereby first connecting other portions of the inner circumference edge 71 together.

After the first suture 80 is secured across the opening 73 of the vaginal cuff 70, a plurality of additional sutures 86 are sewn through the vaginal cuff 70 to close the vaginal cuff 70 and bring parts of the inner circumference edge 71 together. The additional sutures 86 extend from the middle 82 to the sides 84 of the vaginal cuff.

Each component of the apparatus 20 may be formed of a biocompatible material, such as any metal or plastic material that is biocompatible. The probes 32A, 32B, and other components, may be formed of a shape memory material, such as Nitinol, as explained above.

The description of the invention is merely exemplary in nature and variations that do not depart from the gist of the invention are intended to be within the scope of the invention. Such variations are not to be regarded as a departure from the spirit and scope of the invention. For example, variations in the various figures can be combined with each without departing from the spirit and scope of the present disclosure.

The preferred embodiment of the present invention has been disclosed. A person of ordinary skill in the art would realize, however, that certain modifications would come within the teachings of this invention. Therefore, the following claims should be studied to determine the true scope and content of the invention.

Any numerical values recited in the above application include ail values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints, the use of "about" or "approximately" in connection with a range apply to both ends of the range. Thus, "about 20 to 30" is intended to cover "about 20 to about 30", inclusive of at least the specified endpoints.

The disclosures of all articles and references, including patent applications and publications, are incorporated by reference for all purposes.

The term "consisting essentially of" to describe a combination shall include the elements, ingredients, components or steps identified, and such other elements ingredients, components or steps that do not materially affect the basic and novel characteristics of the combination.

The use of the terms "comprising" or "including" describing combinations of elements, ingredients, components or steps herein also contemplates embodiments that consist essentially of the elements, ingredients, components or steps.

What is claimed is:

1. A method of closing a vaginal cuff of a vaginal canal, the vaginal cuff being formed at a distal end of the vaginal canal and the vaginal canal forming a vaginal opening at a proximal end of the vaginal canal, the method comprising:
   advancing a hollow sleeve member with an open interior section and a sleeve proximal and a sleeve distal end into a patient's anatomy;
   advancing a first probe and a second probe through the open interior section of the hollow sleeve member and into the patient's anatomy through the sleeve distal end, the first probe having a first tissue manipulator disposed at a probe distal end of the first probe and the second probe having a second tissue manipulator disposed at a probe distal end of the second probe;
   grasping a first tissue portion of the vaginal cuff with the first tissue manipulator and grasping a second tissue portion of the vaginal cuff with the second tissue manipulator, the first and second tissue portions being spaced apart from each other by a lateral space;
   moving at least one of the hollow sleeve member and the first and second probes relative to each other by advancing the hollow sleeve member toward the vaginal cuff over the first and second probes, thereby bringing together the distal ends of the first and second probes and the first and second tissue portions to reduce or eliminate the lateral space.

2. The method of claim 1, further comprising inserting an outer cannula into the patient's anatomy, the step of advancing the hollow sleeve member including advancing the hollow sleeve member through the outer cannula, wherein advancing the hollow sleeve member toward the vaginal cuff over the first and second probes includes moving the hollow sleeve member axially with respect to the outer cannula.

3. The method of claim 2, wherein the vaginal cuff defines a vaginal cuff plane, the first and second tissue portions being disposed generally within the vaginal cuff plane, the method further comprising holding the first and second probes with respect to the outer cannula after grasping the first and second tissues portions and keeping the first and second tissue manipulators generally within the vaginal cuff plane when the hollow sleeve member is advanced over the first and second probes.

4. The method of claim 3, further comprising suturing the first and second tissue portions together while holding the first and second tissue portions together with the first and second tissue manipulators.

5. The method of claim 4, wherein the step of suturing includes beginning the suturing by fixing a first suture through a first central portion of the first tissue portion and a second central portion of the second tissue portion, thereby connecting the first and second central portions together, the first and second central portions being disposed on opposite sides of the vaginal cuff.

6. The method of claim 5, wherein the first and second probes have a flexible material that is preformed into an arcuate shape.

7. The method of claim 1, wherein the step of advancing the hollow sleeve member into the patient's anatomy includes advancing the hollow sleeve member into the vaginal canal through the vaginal opening.

\* \* \* \* \*